(12) United States Patent
Burian et al.

(10) Patent No.: US 7,820,015 B2
(45) Date of Patent: Oct. 26, 2010

(54) DEVICE FOR RECORDING THE BOILING CURVE OF LIQUIDS

(75) Inventors: Matthias Burian, Strasshof a.d. Nordbahn (AT); Roland Aschauer, Vienna (AT)

(73) Assignee: Grabner Instruments Messtechnik Nfg. Gesellschaft m.b.H. & Co. KG., Vienna (AT)

( * ) Notice: Subject to any disclaimer, the term of this patent is extended or adjusted under 35 U.S.C. 154(b) by 0 days.

(21) Appl. No.: 12/146,881

(22) Filed: Jun. 26, 2008

(65) Prior Publication Data

US 2009/0059995 A1    Mar. 5, 2009

Related U.S. Application Data

(62) Division of application No. 10/511,947, filed as application No. PCT/AT03/00118 on Apr. 23, 2003, now Pat. No. 7,556,716.

(30) Foreign Application Priority Data

Apr. 24, 2002    (AT)    ............................. GM270/2002

(51) Int. Cl.
*B01D 3/42*    (2006.01)
*G01N 25/08*    (2006.01)
*G01N 25/10*    (2006.01)
*G01N 25/14*    (2006.01)

(52) U.S. Cl. ......................... 202/160; 62/3.2; 73/61.77; 73/863.01; 202/267.1; 202/185.3; 374/16; 374/27

(58) Field of Classification Search ................... 62/3.2; 73/61.77, 863.01, 863.12; 202/160, 185.3, 202/267.1, 235; 374/16, 25, 27; 703/138, 703/173
See application file for complete search history.

(56) References Cited

U.S. PATENT DOCUMENTS

| | | | | |
|---|---|---|---|---|
| 3,239,432 | A * | 3/1966 | Rhodes et al. | 202/160 |
| 3,364,731 | A * | 1/1968 | Hook | 73/61.77 |
| 4,250,739 | A * | 2/1981 | Audeh et al. | 374/27 |
| 4,846,935 | A * | 7/1989 | Giesselmann et al. | 203/86 |
| 5,398,806 | A * | 3/1995 | Quinn | 202/83 |
| 6,581,443 | B2 * | 6/2003 | Abaev et al. | 73/61.77 |
| 6,695,951 | B1 * | 2/2004 | Bitterly et al. | 202/182 |

* cited by examiner

*Primary Examiner*—Virginia Manoharan
(74) *Attorney, Agent, or Firm*—Cozen O'Connor

(57) ABSTRACT

A device for recording the boiling curve of liquids, in particular petroleum products, made of a distillation apparatus which includes a distillation column and a condenser, a sample dish connected to the distillation apparatus and a pump connected to the sample dish to fill the sample dish, wherein the filling means and the condenser are made of well heat-conducting material and the filling means and the condenser are connected to a temperature controller.

19 Claims, 1 Drawing Sheet

DEVICE FOR RECORDING THE BOILING CURVE OF LIQUIDS

CROSS-REFERENCE TO RELATED APPLICATIONS

This application is a divisional of co-pending, commonly assigned U.S. patent application Ser. No. 10/511,947, now U.S. Pat. No. 7,556,716, filed Oct. 21, 2004, which is a U.S. National Phase filing of PCT patent application No. PCT/AT03/00118, filed Apr. 23, 2003.

FIELD OF THE INVENTION

The invention relates to a method for recording the boiling curve of liquids, in particular petroleum products and/or solvents, in which a sample amount of the liquid to be analyzed is evaporated and subsequently condensed, wherein the vapor temperature and the respectively evaporated amount of liquid are monitored, and a device for carrying out said method.

BACKGROUND OF THE INVENTION

The distillation properties of liquids and, in particular, petroleum products such as, for instance, fuel are laid down in numerous product specifications. In the case of fuel, it is to be ensured in this manner that engines of the usually occurring capacity and temperature ranges are operated with the appropriate fuels. In this respect, an internationally acknowledged distillation test standard method is available for petroleum products, which is accepted by ASTM and ISO. In that method, 100 ml of the liquid to be analyzed are distilled in a heated distillation flask of glass and condensed in a cooled condenser tube. The condensate is collected in a graduated glass cylinder. Between the onset of boiling and the end of boiling, the temperature of the vapor and the volume condensed up to that point of time are determined (boiling curve). The volume of the distillation residue that remains in the distillation flask after having shut off the heater is determined by the aid of a measuring cylinder, and the boiling curve is corrected accordingly.

That technique was developed around 1920. The control of the heater, the reading of the vapor temperature and the determination of the corresponding condensate volume were carried out by the operator of the device.

U.S. Pat. No. 4,528,635 describes an automatic distillation apparatus. That apparatus employs the same distillation flasks, condensers and glass cylinders as the original, manual method. A device for the determination of the condensed volume as well as a microprocessor controlling heating and cooling and automatically recording measuring data was installed in that apparatus. Basically, the technique remained unchanged though.

That standard technique involves a number of disadvantages for the user. The sample volume is high with 100 ml, the sample and distillation residue have to be dosed and filled manually, the glass flasks and cylinders are fragile and have to be cleaned after every distillation, the measuring time is long, and the apparatus has a large volume and can only be used in laboratories.

SUMMARY OF THE INVENTION

The present invention aims to provide a method and a device which, at substantially smaller structural dimensions, render feasible the realization of the device as a portable device with the method having, at the same time, to be conducted in a manner that any manual influence will be minimized. In addition to the miniaturization and automation sought by the invention, the invention, at the same time, aims to provide results that are equivalent to those of the ASTM standard technique and, due to the largely automated procedure, yield higher degrees of accuracy and reproducibility of the measured results despite a shortened measuring time and a simultaneously reduced amount of sample required. The invention, in particular, aims to enable the fully automatic control of the method and a reduction in terms of structural dimensions, of the overall device required for the realization of the method, so that it can be arranged in a conventional motor vehicle, for instance in the trunk, and supplied with energy by the vehicle network.

To solve this object, the method according to the invention consists essentially in that the sample amount is dosed by a filling means, particularly a pump, that the filling means and the condensate collection chamber are brought to a defined, and preferably identical, temperature level, and that the condensed volume is determined volumetrically in a manner known per se and the distillation residue of the sample amount is determined by weighing. Due to the fact that the sample amount is dosed by a filling means and, in particular, a pump, a first, usually manual influence will be avoided and a high degree of precision will be attained during the charging of the device suited to carry out said method. Simultaneously with the automation of such charging, or dosing of said sample amount, an error source will be eliminated and the exact volume determination of the condensate, or exact determination of the product already distilled out of the sample amount, will be enabled by the filling means and the condensate collection chamber being brought to a defined, and preferably identical, temperature level. Due to the fact that the distillation residue of the sample amount is now determined by weighing, it is feasible to calculate the respective volume units with high precision and, together with the volumetric determination of the condensed volume, ensure with a small sample amount a highly precise measuring result which will be available with high precision and free of distortions caused by manipulations or temperature deviations.

In a particularly simple manner, the method according to the invention is carried out such that the sample amount is pumped into a sample dish which is moved by the aid of a lifting drive into a gas-tight connection with the distillation apparatus and pressed at the same. Such a sample dish in a simple manner can be made of metal and hence designed as a cheap disposable article, as in correspondence with a preferred configuration. As a result, distortions and errors caused by insufficient cleaning of glass hardware will be avoided, since such a cheap and small sample dish can be simply discarded after boiling and a new dish can be readily used for the subsequent assay. The simple mechanical and fully automatic pressing of the sample dish at the distillation apparatus, on the other hand, may also be used to again lower the sample dish after the end of distillation and move it to a weighing device in order to determine the distillation residue with high accuracy.

Particularly simple cleaning and further automation of the method according to the invention will be achieved in that the filling means for the dosing of the sample amount, after completion of the measuring procedure, via at least one valve is switched to remove the condensate by suction, whereby, as already mentioned, cleaning of the sample dish can be obviated if the sample dish is discarded after one-time use, as proposed by the invention.

The thermostatic filling means, thus, not only allows for the precise dosing of the sample amount but, at the same time, also enables the appropriate withdrawal of the distillate and, if necessary, appropriate rinsing or cleaning. Particularly with the preferably used device for the determination of the condensate volume, said pump in a particularly simple manner may also serve to adjust the meniscus, the height of which can subsequently be monitored and evaluated for the volumetric determination of the condensate.

Overall, in the context of the method according to the invention it is preferably proceeded in a manner that sample is used in an amount of from 1 to 12 ml, preferably about 6 ml, that the distillation rate is chosen such that the time between the onset of boiling and the end of boiling is less than 15 minutes, and that the distillation residue determined by weighing is converted to volume, whereby measuring times can be reduced to approximately half of the hitherto known standard measuring times, and less than one tenth of the hitherto used sample liquid volume will do. In this context, the appropriate selection of parameters within the cited limits is essential, since it is feasible within that range of parameters to obtain directly comparable results, which can be directly compared with the known standard measuring curves for distillation tests to the extent these are available in standardized form.

The device according to the invention for carrying out said method is essentially characterized in that a filling means, particularly a pump, for filling in a sample amount is connected with a duct leading to a sample dish, that the filling means just as the distillation apparatus, particularly the condenser, are made of well heat-conducting material, particularly metal, and that the filling means and the condenser are connected to a temperature controller. Due to the fact the filling means just as the distillation apparatus and, in particular, that part of the distillation apparatus in which the volumetric determination of the condensate takes place, namely the condenser, are made of well heat-conducting material, it is feasible to ensure a sufficiently homogenous temperature distribution, and use an adequate high-precision temperature controller, even with particularly small-structured devices. By appropriate thermostatization, it is, thus, feasible even with small-structured devices to keep the respective errors low and enhance the precision of the results so as to enable the realization of an overall portable device. By arranging the sample dish on a movable support connected with an adjustment drive, as in correspondence with a preferred further development, it has become feasible to use a cost-effective alternative for glass containers and, in particular, discard such a sample dish after one-time use, the latter constituting a sufficiently cheap structural component. The sample dish in this case can be positioned against the distillation apparatus by the aid of the adjustment drive and connected with the distillation apparatus in an accordingly gas-tight manner by pressing, while it is, at the same time, appropriately heated in order to enable distillation to occur. Furthermore, the movable adjustment drive allows the sample dish to be again withdrawn at the end of boiling and moved to a weighing means in order to enable the respective determination of the distillation residue with high precision.

With a view to providing a small-structured portable device capable of being energized by simple battery operation, the configuration advantageously is devised such that the temperature controller is designed as an electric cooler and/or heater using, in particular, Peltier elements. Such Peltier elements are usually poled to be used as a cooling means. Under unfavorable weather conditions, an accordingly higher temperature may, however, be selected by pole reversal in order to obtain results comparable to those of standard tests.

A completely autonomous and portable device will result if the filling means and the distillation apparatus are arranged in a common portable housing.

The respective compensation or correction of the volumetric measurements may be ensured in a simple manner in that temperature sensors are provided in both the filling means and the condenser.

The adjustment drive for the sample dish in a simple manner may be designed as a geared motor, thus safeguarding also an appropriate pressing pressure upon lifting of the sample dish. In order to obtain tight sealing between the sample dish and the distillation column, the configuration advantageously is devised such that the edge of the sample dish and the edge of the connection opening of the distillation column are designed to be conical, hollow-conical or ball-shaped, so as to ensure the gas-tight connection of the sample dish with the distillation apparatus while applying the pressing pressure created by the adjustment drive.

In order to reliably avoid also in this case thermal errors that might lead to distortions of measurements, the configuration advantageously is devised such that the distillation column is surrounded by an insulation means.

A particularly advantageous configuration of the volumetric measuring device in a distillation apparatus substantially comprised of metal will be achieved in that, as in correspondence with a preferred configuration, the condenser comprises an axial zone with reduced diameter of a material transparent to light and, in particular, infrared light, particularly glass, which is followed by a zone having a larger clear width adapted to receive an axially movable piston. Such a zone formed, for instance, of glass tubes may have an accordingly small clear cross section so that even slight volume changes will bring about respective changes in the liquid level or meniscus, respectively. Yet, in order to be still able to receive an accordingly increased amount of condensate, such a glass tube will be followed by the axially movable piston in a cylinder having an accordingly larger clear width, whereby measurements may be effected in a simple manner by measurements of the adjustment path of the piston, from which the respective volume can be concluded. To this end, the configuration advantageously is devised such that the axially movable piston is connected with an adjustment drive, particularly a stepper motor or geared motor including a rotary encoder, which is actuatable as a function of the signals transmitted by an optical detector, the optical signal transmitter being preferably arranged in the region of the axial zone of light-transparent material and designed for the detection of the meniscus of the condensed liquid, and that the adjustment drive of the piston is actuatable for the correction of the position of the meniscus.

As already pointed out, the distillation apparatus in a particularly simple manner may be made of special steel, brass or titanium, and the dish may be made of metal, preferably aluminum or copper. Such a configuration is characterized by an accordingly cost-effective design of the sample dish while providing a simultaneously simple homogenous temperature distribution.

The ASTM standard technique is designed for a distillation test under atmospheric pressure. Consequently, the configuration in an advantageous manner is devised such that a pressure sensor, particularly a piezoresistive pressure sensor, is provided for the determination of the air pressure, and that the distillation apparatus in the region of the condenser is designed with an open connection to the atmosphere so as to enable, at any time, an accordingly compensating calculation based on the pressure values measured. The complete detection of all measuring values in the same device and, in particular, also the weight detection of the distillation residue contained in the sample dish will advantageously be feasible, if the configuration is devised such that a weighing means is arranged within the housing.

The fully automatic realization of the method to be carried out in the context of a device of this type is feasible in a particularly simple manner, if the measuring values are fed via lines to a microprocessor and a display or output means for the measuring results is provided.

DETAILED DESCRIPTION OF THE INVENTION

Figure 1:
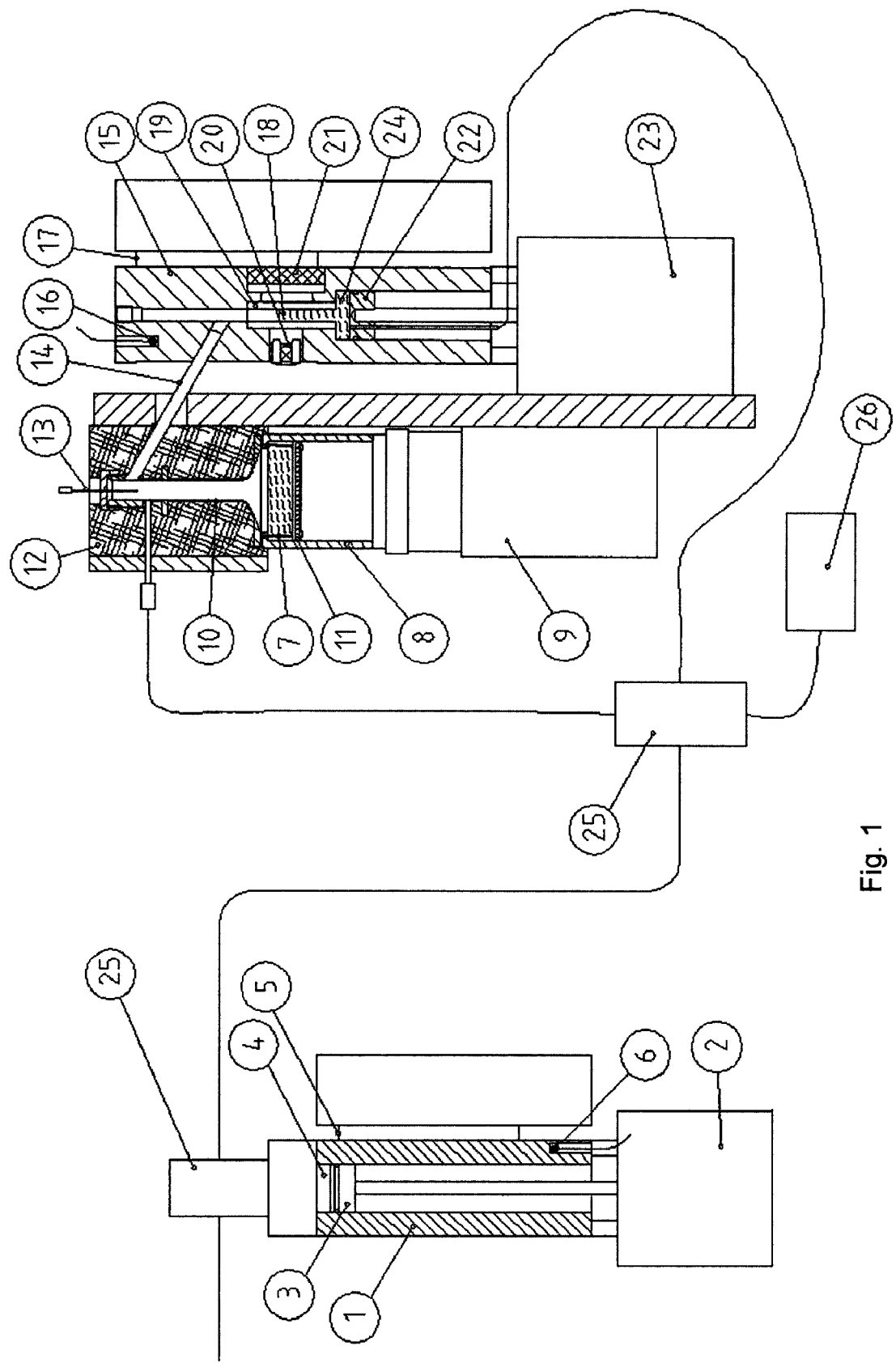
FIG. 1 is a schematic diagram of a device and method according to the present invention, particularly a filling means and a sample dish.

In the following, the invention will be explained in more detail by way of an exemplary embodiment of the device according to the invention schematically illustrated in FIG. 1 as well as the pertinent method description.

The filling means 1 is comprised of a first piston 3 driven by a stepper motor or geared motor including a rotary encoder 2, which piston is moved within a nickel-plated aluminum chamber 4 and sealed by the aid of an 0-ring. The volume resolution is better than 1ul. The temperature of the filling means 1 ids controlled by the aid of a Peltier element 5 and measure by means of a temperature sensor 6, preferably a Pt-100-resistance sensor.

The filling means 1 is comprised of a piston 3 driven by a stepper motor or geared motor including a rotary encoder 2, which piston is moved within a nickel-plated aluminum chamber 4 and sealed by the aid of an O-ring. The volume resolution is better than 1 ul. The temperature of the filling means 1 is controlled by the aid of a Peltier element 5 and measured by means of a temperature sensor 6, preferably a Pt-100-resistance sensor.

The sample dish 7 is made of deep-drawn aluminum. It is, therefore, cheap and will be discarded after measuring so as to avoid cumbersome cleaning. The sample dish 7 is pressed at the precious-steel distillation column 10 via a support 8 which can be moved by the aid of a drive motor 9. In the support 8, an electric heater 11 is integrated too. Turned onto the distillation column 10 is a chamfered ring against which the sample dish is pressed. Thereby, an air-tight measuring chamber is formed. The distillation column 10 is externally insulated by the aid of mineral wool 12 so as to avoid any influence on the vapor temperature caused by differences in the ambient temperature.

The vapor temperature is determined by the aid of a thermocouple 13. Laterally on the distillation column 10 is located an outlet 14 which opens into the condenser 15. The condenser 15 is made of aluminum and is upwardly open such that the distillation will proceed under the prevailing air pressure. The condenser temperature is measured by the aid of a temperature sensor 16, preferably a PT-100 resistance thermometer, and kept constant by the aid of a Peltier element 17.

Incorporated in the condenser is a volume detection system 18. This system is comprised of a glass tube 19 which is installed in the condenser and whose temperature, therefore, equals that of the condenser 15. The glass tube 19 is illuminated by two LEDs 20 forming approximately parallel beams. An optical line detector 21 (preferably a photodiode array) is attached in a manner that the diodes will rest in the focus of the cylinder lens forming the glass tube 19 when filled with sample. If the glass tube 19 is filled with liquid up to approximately one half, the light beam of the LEDs 20 is focused onto the line detector 21 in the region where the liquid is contained. No such cylinder lens effect occurs above the liquid-air interface (meniscus). The detector 21 will, therefore, register an elevated light intensity below the meniscus, while the intensity will be lower above the meniscus.

If the meniscus in the glass tube 19 rises, this will also cause a change in the intensity distribution on the line detector 21. The position resolution for the determination of the position of the meniscus is better than 0.6 mm.

The position of the meniscus may be changed by the second piston 22, which is moved in a cylindrical chamber 24 by a stepper motor or a geared motor including a rotary encoder 23. Any change in the height of the meniscus after a movement of the second piston 22 is determined by the line detector 21.

If vapor is condensed in the condenser, the meniscus in the glass tube 19 will rise. As this rise reaches a pregiven value, the second piston 22 is moved downwards by a predetermined amount, thus causing the meniscus to sink again. In this manner, the meniscus will always be kept within the reach of the line detector 21.

The position of the meniscus may be changed by the piston 22, which is moved in a cylindrical chamber 24 by a stepper motor or a geared motor including a rotary encoder 23. Any change in the height of the meniscus after a movement of the piston 22 is determined by the line detector 21.

If vapor is condensed in the condenser, the meniscus in the glass tube 19 will rise. As this rise reaches a pregiven value, the piston 22 is moved downwards by a predetermined amount, thus causing the meniscus to sink again. In this manner, the meniscus will always be kept within the reach of the line detector 21.

The volume of the condensed sample is determined from the known inner diameter of the glass tube 19 and the change in the meniscus height. The volume resolution in this case is better than 10 ul, amounting to at least 0.1% of the filling volume.

Valves 25 serve to distribute the sample within the apparatus. A waste container 26 serves to collect the used samples.

All sensors, motors, Peltier elements, valves and the heating are controlled and monitored by a microprocessor in a manner that the measuring procedure will run fully automatically according to a predetermined program without intervention of an operator.

The whole device can be incorporated in a portable housing.

Measuring Procedure:

At the beginning of a measurement, a fresh sample dish 7 is placed on the support 8 and thereby pressed against the distillation column 10 by the aid of a motor 9. The filling means 1 and the condenser 15 are held at the same temperature. Sample is then sucked in by the filling means 1. A predetermined volume, preferably 6 ml, is dosed into the sample dish 7. Likewise, a small volume is filled into the volume detection system 18 such that the meniscus in the glass tube 19 will be located in the detection range of the line detector 21.

The heater 11 is then turned on. Shortly afterwards, the sample starts to boil and evaporate. The temperature of the rising vapor is continuously measured by the thermocouple 13. The heater capacity is a function of this vapor temperature and is controlled by the microprocessor so as to increase with the vapor temperature rising.

The vapor enters the condenser 15 through the outlet 14 and there condenses a second time. The condensed volume is constantly measured by the volume detection system 18.

With the sample having been evaporated completely, the supply of vapor is stopped and the temperature of the thermocouple 13 will decrease. After this, the heater 11 is turned off. As soon as the temperature has fallen below a threshold value, the support 8 carrying the sample dish 7 is moved downwards, and the sample dish can be removed, weighed and then discarded. The used sample in the condenser 15 is sucked off via the filling system 1 and filled into the waste container 26.

The weight of the sample dish containing the residue is input. From this, the distillation residue is calculated by the microprocessor and the boiling curve is corrected accordingly. The measuring results can be visualized on an incorporated display, printed or transferred to a computer.

The overall measuring time amounts to approximately half of the time necessary for the ASTM standard method.

The invention claimed is:

1. A device for recording the boiling curve of liquids which comprises:
    a distillation apparatus comprising a distillation column (10) and a condenser (15);
    a sample dish (7) connected to the distillation apparatus;
    a filling means (1) connected to the sample dish (7) to fill the sample dish (7); and
    a temperature controller connected to the filling means (1) and the condenser (15),
    wherein the filling means (1) and the condenser (15) comprise material that conducts heat well,
    wherein the condenser (15) comprises an axial zone with reduced diameter of a material transparent to light, which is followed by a zone having a larger inner diameter, an axially movable piston (22) being received in said zone having a larger inner diameter.

2. The device according to claim 1, wherein the sample dish (7) is arranged on a movable support (8), which is connected with an adjustment drive (9), by which an edge of the sample dish (7) can be pressed at an edge of a connection opening of the distillation column (10) that follows the sample dish (7).

3. The device according to claim 2, wherein the adjustment drive (9) for the sample dish (7) is designed as a geared motor.

4. The device according to claim 2, wherein the edge of the sample dish (7) and the edge of the connection opening of the distillation column (10) are designed to be conical, hollow-conical or ball-shaped, so as to ensure the gas-tight connection of the sample dish (7) with the distillation apparatus while applying the pressing pressure created by the adjustment drive (9).

5. The device according to claim 2, wherein the distillation column (10) is surrounded by an insulation means (12).

6. The device according to claim 1, wherein the temperature controller is designed as an electric cooler and/or heater.

7. The device according to claim 6, wherein Peltier elements (5, 17) are used for the electric cooler and/or heater.

8. The device according to claim 1, wherein temperature sensors (6, 16) are provided in both the filling means (1) and the condenser (15).

9. The device according to claim 1, wherein the axially movable piston (22) is connected with an adjustment drive, which is actuatable as a function of the signals transmitted by an optical detector (21).

10. The device according to claim 1, wherein an optical signal transmitter (20) is arranged in the region of the axial zone of light-transparent material and designed for the detection of a meniscus of a condensed liquid, and wherein the adjustment drive of the piston (22) is actuatable for the correction of the position of the meniscus.

11. The device according to claim 1, wherein the distillation apparatus is made of steel, brass or titanium, and the sample dish (7) is made of metal.

12. The device according to claim 1, further comprising a pressure sensor arranged for the determination of an air pressure, and wherein the distillation apparatus in a region of the condenser (15) is designed with an open connection to the atmosphere.

13. The device according to claim 12, wherein the pressure sensor is designed as a piezoresistive pressure sensor.

14. The device according to claim 1, wherein a weighing means designed for the weighing of a distillation residue of the sample amount is arranged within a housing.

15. The device according to claim 1, wherein measuring values are fed via lines to a microprocessor designed for the evaluation and calculation of measuring results, and that a display or output means for the measuring results is provided.

16. The device according to claim 1, wherein the material transparent to light is glass.

17. The device according to claim 1, wherein the adjustment drive is designed as a stepper motor or geared motor including a rotary encoder (23).

18. The device according to claim 1, wherein the the sample dish (7) is made of aluminum or copper.

19. The device according to claim 1, wherein a pump is used as said filling means (1).

* * * * *